United States Patent
Parks et al.

(10) Patent No.: US 8,901,163 B2
(45) Date of Patent: Dec. 2, 2014

(54) METHOD OF TREATING HYPERESTHESIA, PARESTHESIA, DOLOR, AND PRURITUS CAUSED BY INSECT STINGS OR NOXIOUS WEEDS OR PLANTS USING AVERMECTIN COMPOUND

(75) Inventors: Jeffrey D. Parks, Ormond Beach, FL (US); L. Dean Parks, Ocala, FL (US)

(73) Assignee: Galderma S.A., Lausanne (CH)

( * ) Notice: Subject to any disclaimer, the term of this patent is extended or adjusted under 35 U.S.C. 154(b) by 1755 days.

(21) Appl. No.: 11/648,941

(22) Filed: Jan. 3, 2007

(65) Prior Publication Data
US 2008/0161384 A1 Jul. 3, 2008

(51) Int. Cl.
*A61K 31/366* (2006.01)
*A61P 17/00* (2006.01)

(52) U.S. Cl.
CPC ..................... *A61K 31/366* (2013.01)
USPC ......................................................... 514/450

(58) Field of Classification Search
CPC .................................................. A61K 31/366
See application file for complete search history.

(56) References Cited

U.S. PATENT DOCUMENTS

| | | | |
|---|---|---|---|
| 5,952,372 A | 9/1999 | McDaniel | |
| 6,133,310 A | 10/2000 | Parks | |
| 6,319,945 B1 | 11/2001 | Parks | |
| 6,399,651 B1 | 6/2002 | Parks | |
| 6,399,652 B1 | 6/2002 | Parks | |
| 6,433,006 B2 | 8/2002 | Parks | |
| 2004/0167084 A1* | 8/2004 | Parks | 514/28 |

OTHER PUBLICATIONS

Chosidow "Scabies and pediculosis" The Lancet, 355, 2000, 819-26.*

Peate ("Occupational Skin Disease" American Family Physician, 66(6), 2002, 1025-1032).*
Steen et al. ("Arthropods in Dermatology" Journal of the American Academy of Dermatology, 50(6), 2004, 819-842).*
International Search Report of PCT/US2008/000007, issued Jul. 28, 2008.
International Preliminary Report on Patentability (Chapter I) of PCT/US2008/000007, issued Jul. 7, 2009.
European Search Report of regional phase application of PCT/US2008/000007, issued Nov. 26, 2009.
Jenkins E.J. et al.: Development and pathogenesis of *Parelaphostrongylus odocoilei* (nematoda: protostrongylidae) in experimentally infected thinhorn sheep (*Ovis dalli*). Journal of Wildlife Diseases vol. 41, No. 4, Oct. 2005, pp. 669-682, XP008111187.
Leo'n-Vizcai'no L. et al.: 'Experimental ivermectin treatment of sarcoptic manage and establishment of a mange-free population of Spanish ibex'. Journal of Wildlife Diseases vol. 37, No. 4, Oct. 2001, pp. 775-785, XP008111188.
Hengge U.R. et al.: 'Scabies: a ubiquitous neglected skin disease'. The Lancet Infectious Disease vol. 6, No. 12, Dec. 2006, pp. 769-779, XP005774623.
Stibich, Adam S. MD; Yagan, Mark MD; Sharma, Vidya MD; Herndon, Betty PhD; Montgomery, Christopher MS: 'Cost-effective post-exposure prevention of poison ivy dermatitis'. Interntional Journal of Dermatoloby, [Online] vol. 39, No. 7, Jul. 2000, pp. 515-518, XP002556566 Retrieved from the Internet: URL:http://www3.interscience.wiley.com/cgi-bin/fulltext/120189105/HTMSTARTW> [retrieved on Nov. 20, 2009].

* cited by examiner

*Primary Examiner* — Kortney L Kinkel
(74) *Attorney, Agent, or Firm* — CUSPA Technology Law Associates, P.A.; Yi Li

(57) ABSTRACT

A method of treating hyperesthesia, paresthesia, dolor, and pruritus caused by an insect or arthropod sting or bite, or a skin contact with a noxious weed or plant is disclosed. The method includes topically applying a dermatological composition containing an avermectin compound to an affected area immediately after said sting or bite, or said skin contact occurs. The method further includes moistening the affected area first prior to application of the dermatological composition.

24 Claims, No Drawings

METHOD OF TREATING HYPERESTHESIA, PARESTHESIA, DOLOR, AND PRURITUS CAUSED BY INSECT STINGS OR NOXIOUS WEEDS OR PLANTS USING AVERMECTIN COMPOUND

FIELD OF THE INVENTION

The present invention relates to methods for treating hyperesthesia, paresthesia, dolor and pruritus caused by insect or arthropod stings or bites, or skin contact with noxious weeds or plants.

BACKGROUND OF THE INVENTION

Insect or arthropod stings or bites are commonly occurring instances in human life, particularly in the rural areas. Stings or bites are usually caused by midges, biting flies, bees, wasps, such as yellow jacket and hornet, fire ants, spiders, etc. The stings or bites cause intense stinging, burning, pain, itching and tingling sensations. Clinically, these symptoms are referred to as hyperesthesia, paresthesia, dolor, and pruritus. Typically, after stung, the skin becomes red and swollen, and welting or pustule will form. Pustule is a small collection of pus in the top layer of skin (epidermis) or beneath it in the dermis. Pus is a mixture of inflammatory cells and liquid.

Currently, there is no effective medication for treating the intense stinging, burning, pain, itching and tingling sensations caused by the sting. It is typically recommended to immediately wash the stung area with soap and water, then cool off the skin with ice cubes or an ice-pack that has been wrapped in a cloth or thin towel, and rest the affected area and elevate it if possible to prevent excessive swelling. It is also recommended to use a painkilling cream or gel or an antihistamine to soothe the itch. However, the pain and burning sensations can be so intense, currently no topical medication stops the pain effectively. To the level of the pain reduction that the medicine can achieve, it will only last for a period of time because it merely numbs the affected area temporarily, but does not affect the cause of these symptoms.

On the other hand, skin contact with fireweed, stinging nettle, rhus plants or other noxious weeds or plants can also cause intense stinging, burning, pain, and itch, and frequently welting or pustules will form. Current treatments typically include topical application of an antihistamine, or cortisone cream to reduce the symptoms. Frequently, these are not effective to alleviate the symptoms caused by the noxious weeds or plants. The patients can suffer from severe discomfort for days after occurrence of the instance.

In the situation of either severe stings, or an extensive skin contact with noxious weeds or plants, frequently the patients have to go the emergency room for treatment.

The avermectin family of compounds is a series of very potent antiparasitic agents known to be useful against a broad spectrum of endoparasites and ectoparasites in mammals and also to have agricultural uses against various nematode and insect parasites found in and on crops and in soil. Ivermectin is a member of the avermectin family; it has been used as an antiparasitic agent to treat various animal parasites and parasitic diseases since mid-1980's. It is commercially available for animal use as Cardomec (for felines), Zimecterin (for equines) and Ivomec (for bovines) by MERIAL Limited, Duluth, Ga. The medicine is available in tablets, paste, or chewables for heartworm prevention, topical solution for ear mite treatment, or as oral or injectable solution for other parasite problems.

Ivermectin is also commercially available from Merck & Co., Inc for human use as Stromectol® for eradication of threadworm Strongyloides stercoralis, and for eradication of Onchocerca volvulus. The medicine is available in tablets and is orally administered by the patients.

Magda et al. Amer. J. Trop. Med. Hyg. 53(6) 1995 pp. 652-653 describe a method of topical application of ivermectin to treat head lice. Ivermectin is found to have a curative effect after a single topical application. U.S. Pat. No. 5,952,372 (to McDaniel) discloses a method of treating a form of rosacea associated with the ectoparasite Demodex by orally administering or topically applying ivermectin to fill and eliminate Demodex Follicuorum mites from hair follicles in affected skin.

U.S. Pat. Nos. 6,133,310, 6,433,006, 6,399,652, 6,399,651 and 6,319,945 (to Parks) disclose methods of treating acne rosacea, seborrheic dermatitis, acne vulgaris, transient acantholytic dermatitis, acne miliaris necrotica, acne variolifor- mis, perioral dermatitis, and acneiform eruptions by topically applying an avermectin compound, particularly ivermectin, to the affected areas.

None of the above described parasitic diseases and dermatological conditions are related to the hyperesthesia, paresthesia, dolor, and pruritus caused by insect or arthropod stings or bites, or skin contact with noxious weeds or plants. Insect or arthropod stings, or skin contact with noxious weeds or plants are common public problems. Therefore, there is a need for new and effective topical treatments for these conditions, particularly a treatment which can be applied immediately after the instance to reduce the suffering of a patient and to prevent further complications.

SUMMARY OF THE INVENTION

In one embodiment, the present invention is directed a method of treating hyperesthesia, paresthesia, dolor and pruritus caused by insect or arthropod stings or bites, or skin contact with noxious weeds or plants, which comprises topically applying a therapeutically effective amount of an avermectin compound to affected areas of a mammal immediately after the sting or bite, or the skin contact with a noxious weeds and plant occurs. Preferably, the affected area is moistened first, prior to the application of the avermectin compound.

The avermectin compound is in a dermatological composition comprising an effective amount of the avermectin compound and a pharmaceutically acceptable carrier or medium, such as lotions, creams, gels, emulsions, and sprays. The dermatological composition can also be integrated into medicated tape, topical dressing, or dermal patch. The avermectin compound includes avermectins, avermectin derivatives, ivermectin and ivermectin derivatives. The concentration of the avermectin compound in the dermatological composition is from about 0.05% to about 3% (w/w). In a preferred embodiment, ivermectin is used.

In an additional embodiment, the present invention further relates to a dermatological kit for treating hyperesthesia, paresthesia, dolor, and pruritus caused by insect or arthropod stings or bites, or skin contact with noxious weeds or plants. The kit includes a dermatological composition comprising an avermectin compound and a pharmaceutically acceptable carrier in a container, and optionally moistened gauges in a sealed package. The kit further includes an insert with instructions on how to use the dermatological composition for treating hyperesthesia, paresthesia, dolor and pruritus caused by insect or arthropod stings or bites, or skin contact with noxious weeds or plants.

DETAILED DESCRIPTION OF THE INVENTION

The present invention relates to a method of treating hyperesthesia, paresthesia, dolor, and pruritus caused by insect or arthropod stings or bites, or skin contact with noxious weeds or plants. The method comprises topical application of a therapeutically effective amount of an avermectin compound to affected areas of a mammal immediately after the sting or bite, or the skin contact with a noxious weeds and plant occurs.

The insects or arthropods referred herein include noxious insects or arthropods, including, but are not limited to, bees, wasps, such as yellow jacket and hornet, fire ants, midges, biting flies, spiders, and the like. The noxious weeds or plants include, but are not limited to, fireweed, sting nettle, rhus plants and others.

The terms of "hyperesthesia, paresthesia, dolor, and pruritus" used herein refer to the stinging, burning, pain, itching and tingling sensations caused by insect or arthropod stings or bites, or skin contact with noxious weeds or plants, hence, they are used interchangeably. The phrase "immediately after" means to topically apply the avermectin compound to the affected areas as soon as possible, preferably about 2 to about 15 minutes, more preferably, about 2 to about 5 minutes after the occurrence of the instance.

The avermectin compounds for the purpose of the present invention include avermectin, avermectin derivatives, ivermectin, and ivermectin derivatives. The avermectin compound is preferably mixed with a pharmaceutically acceptable carrier or a medium which is suitable for topical application to dermal tissues, to form a dermatological composition.

Preferably, ivermectin is used in the dermatological composition. Ivermectin is a semi-synthetic derivative of avermectin and is generally produced as a mixture of at least 80% 22,23-dihydroavermectin $B_{1a}$ and less than 20% 22,23-dihydroavermectin $B_{1b}$. The following molecular structure represents the avermectin series of compounds, which can be chemically converted to useful derivatives as discussed below.

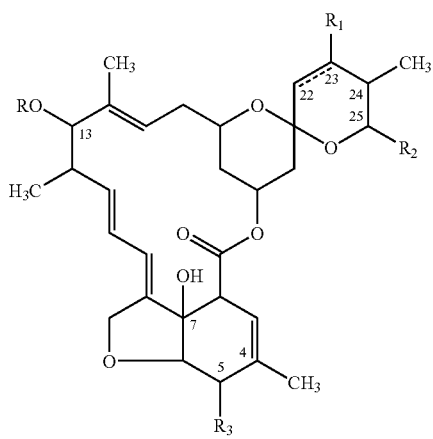

wherein R is the 4'-(alpha-L-oleandrosyl)-alpha-L-oleandrose group of the structure:

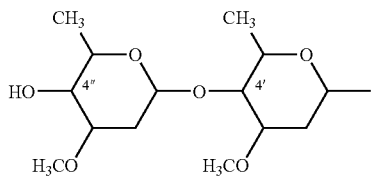 [SMILES: COC1CC(OC2C(C)OC(C)CC2OC)OC(C)C1O]

wherein the broken line indicates a single or double bond; $R_1$ is hydroxy and is present only when said broken line indicates a single bond; $R_2$ is isopropyl or sec-butyl; and $R_3$ is methoxy or hydroxy.

The avermectins, of which ivermectin, a chemically produced analog, is a member, are a series of compounds isolated from the fermentation broth of a C-076 producing strain of *Streptomyces avermitillis* and also chemically produced derivatives thereof. There are eight different but closely related compounds are produced by *S. avermitillis*, designated as $A_{1a}$, $A_{1b}$, $A_{2a}$, $A_{2b}$, $B_{1a}$, $B_{1b}$, $B_{2a}$, and $B_{2b}$. The production of these compounds is described in U.S. Pat. No. 4,310,519. The preparation of ivermectin is disclosed in U.S. Pat. No. 4,199,569. The disclosures of each of the foregoing patents are incorporated herein by reference in their entirety.

Some of the avermectins contain a 22, 23-double bond. This may be selectively reduced to prepare the ivermectin compounds. In addition, the avermectins possess a disaccharide moiety at the 13-position consisting of the alpha-L-oleandrosyl-alpha-L-oleandrosyl group. One or both of these saccharide groups may be removed as described in U.S. Pat. No. 4,206,205, and the produced aglycone derivatives have a hydroxy group at the 13-position. This group may be removed to form the 13-deoxy compound as described in U.S. Pat. Nos. 4,171,314 and 4,173,571; the latter patent also describes the 13-halo derivatives. The avermectin compounds and derivatives have several hydroxy groups which may be acylated as described in U.S. Pat. No. 4,201,861. U.S. Pat. No. 5,055,454 describes invert position 13 of avermectin from a normal alpha stereochemistry to the epimeric 13-beta stereochemistry. U.S. Pat. No. 5,077,308 describes avermectin aglycone derivatives which incorporate a ketal at position 13. U.S. Pat. No. 5,162,363 describes avermectin derivatives where the 23-position ring carbon atom is replaced with sulfur atom. U.S. Pat. No. 5,229,416 describes avermectin aglycone derivatives which incorporate two fluorine atoms at position 13 and 23. U.S. Pat. No. 5,262,400 describes avermectin compounds that have various substituents at the 4a-position including alkyl, alkoxy alkyl, or polyalkoxy alkyl groups. Other derivatives of avermectin and ivermectin are disclosed in U.S. Pat. Nos. 4,333,925, 4,963,667, 5,114,930, 5,350,742, and 5,830,875. All the aforementioned patents are incorporated herein by reference.

All avermectin compounds mentioned and referred to above share the spectrum of anti-parasitic biological activity of ivermectin, varying only in degree. It is expected that they also share the activity spectrum of ivermectin needed for them being suitable to use for the purpose of the present invention.

Suitable examples of pharmaceutically acceptable carrier or medium include, but are not limited to, lotions, creams, gels, emulsions, and sprays suitable for topical application for human skin. These media are well known to those skilled in the art. Preferably, the dermatological compositions include one or more moisturizing agents. "Moisturizing agent," as used herein, is used to include any agent that facilitates hydration of the skin by inhibiting or preventing loss of water from the skin, absorbs water from the atmosphere and hydrates the skin, or enhances the skin's own ability to absorb water directly from the atmosphere, or a combination thereof. Without wishing to be bound by theory it is believed that the moisturizing agent also improves the skin's ability to absorb the avermectin compound. Suitable moisturizing agents include, but are not limited to, hydrophobic agents, and hydrophilic agents, or combinations thereof. Moisturizing agent, when used, are typically present in an amount from about 0.01 to 20 weight percent, preferably about 0.05 to 10 weight percent of the composition. Various moisturizing agents are known and have been used commercially in facial, body and hand creams or lotions.

Preferably, the carrier or medium are free of fragrance, mineral oil, and petrolatum, because mineral oil and petrolatum tend to clog the pores and fragrance tends to cause skin irritation. Using a dermatological composition substantially free these materials is to avoid secondary dermatoses which can be caused by the medium.

Examples 1 to 2 provide exemplary topical dermatological compositions containing an avermectin compound for treating hyperesthesia, paresthesia, dolor, and pruritus caused by insect or arthropod stings or bites, or skin contact with noxious weeds or plants. In Example 2, a commercially available moisturizing lotion manufactured by Galderma Laboratories, Inc. under the trade name Cetaphil® is used as the carrier for ivermectin. Cetaphil® contains purified water, glycerin, hydrogenated polyisobutene, cetearyl alcohol and ceteareth-20, macadamia nut oil, dimethicone, tocopheryl acetate, stearoxytrimethylsilane and stearyl alcohol, panthenol, farnesol, benzyl alcohol, phenoxyethanol, acrylates/C10-30 alkyl acrylate crosspolymer, sodium hydroxide, and citric acid. Cetaphil® is free of fragrance, mineral oil, and petrolatum.

Furthermore, the dermatological composition containing an avermectin compound can be integrated into topic dressing, medicated tape, or dermal patch. Optionally, a combination of different forms of topical treatment can also be used. For example, the medicated tape, or topic dressing can be used for a longer period of time, such as for the night, and the cream or lotion can be used during the day.

In a preferred embodiment, ivermectin is used because it is readily available commercially. The concentration of ivermectin in the dermatological composition for the purpose of the present invention can be in a broad range from about 0.05% to 3% weight by weight (w/w). It has been found that a lotion or a cream containing ivermectin at a concentration as low as 0.07% is clinically effective, as illustrated in the examples hereinafter, in treating hyperesthesia, paresthesia, dolor, and pruritus caused by insect or arthropod stings or bites, or skin contact with noxious weeds or plants.

Ivermectin has been used as an oral medication for treatment of river blindness in human caused by Onchocerca volvulus parasite since late 1980s. With an oral dosage of a moderate ivermectin concentration, this medicine is safe in human, without serious adverse side effects. Therefore, topical treatment of the present invention using ivermectin dermatological composition is safe to human patients, which was also demonstrated by the clinical examples described hereinafter. Furthermore, as discussed previously that a dermatological composition having ivermectin concentration as low as 0.07% is clinically effective in treating hyperesthesia, paresthesia, dolor, and pruritus caused by insect or arthropod stings or bites, or skin contact with noxious weeds or plants. Such a low concentration is advantageous because it reduces risks of adverse side effects, and reduces the possibility of triggering body's autoimmune responses.

Preferably, the method of treatment of the present invention includes moistening the sting or affected areas prior to topically apply the dermatological composition of the present invention. It has been found that topical application of the dermatological composition to damp skin is more effective than applying it on dry skin. After moistening the skin, the dermatological composition can be applied immediately.

Examples 3 to 7 illustrates the effectiveness of the method of the present invention in treating hyperesthesia, paresthesia, dolor, and pruritus caused by insect or arthropod stings or bites, or skin contact with noxious weeds or plants. Drastically different from any known method or medication that has been traditionally used for treating these symptoms, it has been found surprisingly that when the ivermectin lotion is applied on the stung or affected areas immediately after the instance, typically within 2 to 5 minutes, the stinging, burning, pain, and tingling sensations abate in only a few minutes, typically from 5 to 20 minutes. Typically, itchiness or pruritus takes a longer time to subside. In most of the instances described in the examples, only a single application of the instant dermatological composition was used to achieve a complete resolution of the conditions. In the case of rhus dermatitis caused by skin contact of poison ivy, it was found that the patient's response to the treatment was slower and several applications of the dermatological composition were used, however, the treatment achieved definite resolution of the conditions.

Furthermore, as illustrated in Example 3, the treatment of the present invention is also effective for cats. Hence, the instant method is expected to be effective for dogs and horses, which tend to have the same exposures to human as their companions.

Although the inventor is not bound by any theoretical explanation as to why the composition and the method of the present invention are effective in treating hyperesthesia, paresthesia, dolor, and pruritus caused by insect or arthropod stings or bites, or skin contact with noxious weeds or plants, presentation of certain theoretical understanding may be of value. Based on the clinical observations, it is believed that one reason for the efficacy of the composition and the method of the present invention is due in part to ivermectin's anti-inflammatory effect. It is believed that ivermectin is an anti-inflammatory agent, which blocks certain mediators of inflammation, therefore, diminishes various symptoms caused by inflammation. Moreover, in view of the effect of ivermectin on neural system, it may also have some direct effect on the neural receptors in the skin.

The dermatological composition containing ivermectin can be sold as a kit wherein the composition is packaged in a container. Optionally, the kit can also include moistened gauges in a sealed package for damping the affected areas. Instructions on how to use the dermatological composition in accordance with the present invention are included on or associated with the container, which provides detailed instructions for treating hyperesthesia, paresthesia, dolor, and pruritus caused by insect or arthropod stings or bites, or skin contact with noxious weeds or plants.

Operating with the informed consent of individuals who had been stung by insects or arthropods or came in skin contact with noxious weeds or plants, the individuals were treated with the ivermectin dermatological composition and the method of the present invention. Examples 3 to 7 illustrate clinical effectiveness of the method of the present invention.

EXAMPLE 1

A topical dermatological lotion containing avermectin compound is obtained as follows.

Mix 0.10 g of ivermectin (manufactured by Merck & Co., Inc.) with 2 ml of propylene glycol to dissolve ivermectin. The solution is then mixed sufficiently with 100 mg of Dove sensitive Skin facial lotion (manufactured by Englewood Cliffs, N.J.) to make an ivermectin lotion, wherein the concentration of ivermectin is 0.10% (w/w).

Other suitable composition can be made in accordance with Example 1 which include ivermectin in the following concentrations: 0.05%, 0.075%, 0.2%, 0.5%, 1%, and 3% (w/w).

EXAMPLE 2

A topical dermatological composition containing avermectin compound is obtained as follows.

Mix 0.0374 g of Zimecterin (manufactured by MERIAL Limited, Duluth, Ga.) which contains 1.87% ivermectin, sufficiently with 100 mg of Cetaphil® moisturizing lotion (manufactured by Galderma Laboratories, Inc.) to form an ivermectin lotion. The ivermectin concentration in the formed lotion is 0.07% (w/w).

Other suitable compositions can be made in accordance with Example 2 which include ivermectin in the following concentrations: 0.05%, 0.1%, 0.2%, 0.5%, 1%, and 3% (w/w) with Cetaphil® moisturizing lotion as medium. Other compatible commercial available lotions or creams can also be used as a medium or carrier.

EXAMPLE 3

In several separate instances, individual persons were stung by hornets or wasps on the hands, the fingers, the face or the arms. Within 2 to 5 minutes after the sting occurred, the stung areas of the skin were moistened with water first, then the ivermectin lotion of Example 2 was applied topically on the damp areas. In about 10 to 15 minutes, all stinging, burning, pain, and tingling sensations abated. No welting or pustule formed. No further treatment was given after the single application of the ivermectin lotion.

In another separate instance, a cat's paw was stung by a hornet. Within 2 to 5 minutes after the sting occurred, the cat's paw was moistened with water first, then the ivermectin lotion of Example 2 was applied topically on the damp area. No welting or pustule formed, and in a few minutes the cat calmed down from the pain caused by the sting.

EXAMPLE 4

A man was bitten by fire ants on the feet, the ankles and the hands. Within 2 to 5 minutes after the sting occurred, the stung areas of the skin were moistened with water first, then the ivermectin lotion of Example 2 was applied topically on the damp areas. In less than 10 minutes, all stinging, burning, pain and tingling sensations abated. No welting or pustule formed on the affected areas. No further treatment was given after the single application of the ivermectin lotion.

EXAMPLE 5

A man was bitten by a spider on the arm. Within 2 to 5 minutes after the bite occurred, the bite area of the skin were moistened with water first, then the ivermectin lotion of Example 2 was applied topically on the damp area. In less than 15 minutes, the stinging, burning, pain, and tingling sensations abated. No welting or pustule formed on the affected area. No further treatment was given after the single application of the ivermectin lotion.

EXAMPLE 6

In two separate instances, two people came in skin contact with fire weed or stinging nettle on legs, feet or hands, which caused immediate pain and burning sensation on the affected areas. Within 5 minutes after the skin contact occurred, the affected areas of the skin were moistened with water first, then the ivermectin lotion of Example 2 was applied topically on the damp areas. In less than 15 minutes, all pain and burning sensations abated. No further treatment was given after the single application of the ivermectin lotion.

EXAMPLE 7

A man came in skin contact with poison ivy on the face and hands, which caused rhus dermatitis. Immediately after the skin contact occurred, the affected areas of the skin were moistened with water first, then the ivermectin lotion of Example 2 was applied topically on the damp areas. In a few minutes, the pain and burning sensation reduced. The ivermectin lotion was applied subsequently several times in the next 2 days, which resolved the rhus dermatitis.

In the above described informal trials, no adverse side effects or contra-indications were observed among the patients. The patients had no complaints of skin irritation originating from the treatment. There was no report of increasing skin sensitivity.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth in the Claims appended herewith.

What is claimed is:

1. A method for reducing pain caused by a sting by bees, wasps, hornets, or yellow jackets, comprising topically applying a therapeutically effective amount of an avermectin compound to an affected area of a mammal immediately after said sting by bees, wasps, hornets, or yellow jackets occurs, thereby rapidly abating the pain caused by said sting.

2. The method of claim 1, wherein said topically applying said avermectin compound is within 2 to 15 minutes after said sting occurs.

3. The method of claim 2, wherein said topically applying said avermectin compound is within 2 to 5 minutes after said sting occurs.

4. The method of claim 1 further comprising topically applying said avermectin compound to said affected area of said mammal subsequently as needed.

5. The method of claim 1, wherein said avermectin compound is in a dermatological composition comprising an effective amount of said avermectin compound and a pharmaceutically acceptable carrier.

6. The method of claim 5, wherein said avermectin compound is an avermectin, an avermectin derivative, ivermectin, or an ivermectin derivative.

7. The method of claim 6, wherein said avermectin compound is ivermectin in a concentration greater than about 0.05% (w/w) in said dermatological composition.

8. The method of claim 7, wherein said ivermectin is in a concentration range from about 0.05% to about 3.0% (w/w).

9. The method of claim 5, wherein said pharmaceutically acceptable carrier comprises lotions, creams, gels, emulsions, or sprays.

10. The method of claim 5, wherein said dermatological composition is integrated in a medicated tape, topical dressing, or dermal patch.

11. The method of claim 1, wherein said pain caused by said sting is abated in 20 minutes after applying said avermectin compound.

12. The method of claim 1, wherein said pain caused by said sting is abated in 5 minutes after applying said avermectin compound.

13. A method for reducing pain caused by a sting by bees, wasps, hornets, or yellow jackets, comprising the steps of:
   (a) moistening an affected area of a mammal immediately after said sting by bees, wasps, hornets, or yellow jackets occurs; and
   (b) then immediately applying a therapeutically effective amount of an avermectin compound topically to said affected area,
   thereby rapidly abating the pain caused by said sting.

14. The method of claim 13, wherein said moistening said affected area is performed with water.

15. The method of claim 13, wherein said steps (a) and (b) are performed within 2 to 15 minutes after said sting occurs.

16. The method of claim 15, wherein said steps (a) and (b) are performed within 2 to 5 minutes after said sting occurs.

17. The method of claim 13 further comprising topically applying said avermectin compound to said affected area of said mammal subsequently as needed.

18. The method of claim 13, wherein said avermectin compound is in a dermatological composition comprising an effective amount of said avermectin compound and a pharmaceutically acceptable carrier.

19. The method of claim 18, wherein said avermectin compound is an avermectin, an avermectin derivative, ivermectin, or an ivermectin derivative.

20. The method of claim 19, wherein said avermectin compound is ivermectin in a concentration greater than about 0.05% (w/w) in said dermatological composition.

21. The method of claim 20, wherein said ivermectin is in a concentration range from about 0.05% to about 3.0% (w/w).

22. The method of claim 21, wherein said pharmaceutically acceptable carrier comprises lotions, creams, gels, emulsions, or sprays.

23. The method of claim 13, wherein said pain caused by said sting is abated in 20 minutes after applying said avermectin compound.

24. The method of claim 13, wherein said pain caused by said sting is abated in 5 minutes after applying said avermectin compound.

* * * * *